United States Patent [19]
Mao et al.

[11] Patent Number: 6,153,212
[45] Date of Patent: *Nov. 28, 2000

[54] BIODEGRADABLE TEREPHTHALATE POLYESTER-POLY (PHOSPHONATE) COMPOSITIONS, ARTICLES, AND METHODS OF USING THE SAME

[75] Inventors: Hai-quan Mao, Towson; Kam W. Leong, Ellicott City; Zhong Zhao, Ellicott City; Wenbin Dang, Ellicott City, all of Md.; James P. English, Chelsea, Ala.; David P. Nowotnik, Kingsville, Md.

[73] Assignees: Guilford Pharmaceuticals Inc.; Johns Hopkins University School of Medicine, both of Baltimore, Md.

[*] Notice: This patent is subject to a terminal disclaimer.

[21] Appl. No.: 09/165,375

[22] Filed: Oct. 2, 1998

[51] Int. Cl.$^7$ .................. A61F 2/02; A61K 47/30
[52] U.S. Cl. .................. 424/426; 514/772.3
[58] Field of Search .................. 424/426; 514/772.3

[56] References Cited

U.S. PATENT DOCUMENTS

| | | |
|---|---|---|
| 2,891,915 | 6/1959 | McCormack et al. . |
| 3,271,329 | 9/1966 | Coover et al. . |
| 3,442,982 | 5/1969 | Friedman . |
| 3,927,231 | 12/1975 | Desitter et al. . |

(List continued on next page.)

FOREIGN PATENT DOCUMENTS

| | | |
|---|---|---|
| 597473 | 5/1960 | Canada . |
| 2250981 | 10/1997 | Canada . |
| 057 116 | 8/1982 | European Pat. Off. . |
| 0 193 019 | 9/1986 | European Pat. Off. . |
| 0 386 757 | 9/1990 | European Pat. Off. . |
| WO 95/17901 | 7/1995 | WIPO . |
| WO 97/40085 | 10/1997 | WIPO . |
| WO 98/58012 | 12/1998 | WIPO . |

OTHER PUBLICATIONS

Wang, Ya Min, et al., In vitro and in vivo evaluation of taxol release from poly(lactic–co–glycolic acid) microspheres containing isopropyl myristate and degradation of the microspheres, *Journal of Controlled Release*, 49 (1997) 157–166.

Demetrick, Jeffrey S., et al., The Development of a Novel Intraperitoneal Tumor–Seeding Prophylactic, *The American Journal of Surgery®*, vol. 173, May 1997.

(List continued on next page.)

*Primary Examiner*—Carlos A. Azpuru
*Attorney, Agent, or Firm*—Howrey Simon Arnold & White, LLP

[57] ABSTRACT

A medical device is described comprising a biodegradable terephthalate copolymer comprising the recurring monomeric units shown in formula I below:

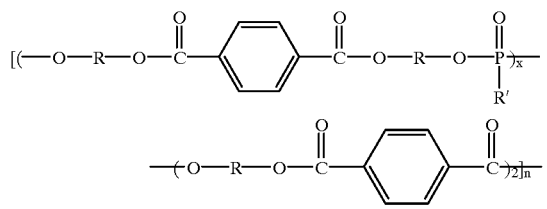

wherein R is a divalent organic moiety; R' is an aliphatic, aromatic, or heterocyclic residue; x is ≧1; and n is 3–7,500, and where the biodegradable terephthalate copolymer is sufficiently pure to be biocompatible and is capable of forming biocompatible residues upon biodegradation. In addition, compositions containing the copolymers and biologically active substances, articles useful for implantation or injection into the body fabricated from the compositions, and methods for controllably releasing biologically active substances using the copolymers, are also described.

59 Claims, 2 Drawing Sheets

U.S. PATENT DOCUMENTS

| | | |
|---|---|---|
| 3,932,566 | 1/1976 | Reader . |
| 4,072,658 | 2/1978 | Okamoto et al. . |
| 4,082,897 | 4/1978 | Hechenbleikner . |
| 4,100,354 | 7/1978 | Owen . |
| 4,156,663 | 5/1979 | Okamoto et al. . |
| 4,259,222 | 3/1981 | Login et al. . |
| 4,315,847 | 2/1982 | Login et al. . |
| 4,315,969 | 2/1982 | Login et al. . |
| 4,328,174 | 5/1982 | Schmidt et al. . |
| 4,374,971 | 2/1983 | Schmidt et al. . |
| 4,463,159 | 7/1984 | Besecke et al. . |
| 4,472,570 | 9/1984 | Besecke et al. . |
| 4,474,937 | 10/1984 | Bales . |
| 4,481,353 | 11/1984 | Nyilas et al. . |
| 4,757,128 | 7/1988 | Domb et al. . |
| 4,789,724 | 12/1988 | Domb et al. . |
| 4,978,332 | 12/1990 | Luck et al. . |
| 5,194,581 | 3/1993 | Leong . |
| 5,213,804 | 5/1993 | Martin et al. . |
| 5,256,765 | 10/1993 | Leong . |
| 5,278,201 | 1/1994 | Dunn et al. . |
| 5,278,202 | 1/1994 | Dunn et al. . |
| 5,304,377 | 4/1994 | Yamada et al. . |
| 5,324,519 | 6/1994 | Dunn et al. . |
| 5,340,849 | 8/1994 | Dunn et al. . |
| 5,399,654 | 3/1995 | Ko et al. . |
| 5,530,093 | 6/1996 | Engelhardt et al. . |
| 5,626,862 | 5/1997 | Brem et al. . |
| 5,952,451 | 9/1999 | Zhao . |

OTHER PUBLICATIONS

Francis, Prudence, et al., Phase I Feasibility and Pharmacologic Study of Weekly Intraperitoneal Paclitaxel: A Gynecologic Oncology Group Pilot Study, *Journal of Clinical Oncology*, vol. 13, No. 12 (Dec.), 1995: pp. 2961–2967.

Hagiwara, Akeo, M.D., et al., Pharmacologic Effects of Cisplatin Microspheres on Peritoneal Carcinomatosis in Rodents, *Cancer*, Feb. 1, 1993, vol. 71, No. 3, pp. 844–850.

Hagiwara, Akeo, et al., Clinical trials with intraperitoneal cisplatin microspheres for malignant ascites—a pilot study, *Anti–Cancer Drug Design* (1993), 8, 463–470.

Höckel, M. et al., Prevention of Peritoneal Adhesions in the Rat with Sustained Intraperitoneal Dexamethasone Delivered by a Novel Therapeutic System, *Annales Chirurgiae et Gynaecologiae* 76: 306–313, 1987.

Jameela, S.R., et al., Antitumour Activity of Mitoxantrone-loaded Chitosan Microspheres Against Ehrlich Ascites Carcinoma, *J. Pharm. Pharmacol.* 1996, 48: 685–688.

Kumagai, Seisuke, et al., Improvement of Intraperitoneal Chemotherapy for Rat Ovarian Cancer Using Cisplatin–containing Microspheres, *Jpn. J. Cancer Res.* 87, 412–417, Apr. 1996.

Owusu–Ababio, G., et al., Efficacy of sustained release ciprofloxacin microspheres against device–associated *Pseudomonas aeruginosa* biofilm infection in a rabbit peritoneal model, J. Med. Microbiol., vol. 43 (1995), 368–376.

Pec, E.A., et al., Biological Activity of Urease Formulated in Poloxamer 407 after Intraperitoneal Injection in the Rat, *Journal of Pharmaceutical Sciences*, vol. 81, No. 7, Jul. 1992.

Sharma, Amarnath, et al., Antitumor Efficacy of Taxane Liposomes on a Human Ovarian Tumor Xenograft in Nude Athymic Mice, *Journal of Pharmacetical Sciences*, vol. 84, No. 12, Dec. 1995.

Kaetsu, Isao, et al., Biodegradable Implant Composites for Local Therapy, *Journal of Controlled Release*, 6 (1987) 249–263.

Zhang, Xichen, et al., Development of Biodegradable Polymeric Paste Formulations for Taxol: An In Vitro and In Vivo Study, *International Journal of Pharmaceutics* 137 (1996) 199–208.

Auerbach, Robert, et al., Site–Specific Drug Delivery to the Lung, *Polymers for Advanced Technologies*, vol. 3, pp. 323–329.

Walter, Kevin A., et al., Intratumoral Chemotherapy, *Neurosurgery*, vol. 37, No. 6, pp. 1129–1145, Dec. 1995.

Burt, Helen M., et al., Controlled Delivery of Taxol from Microspheres Composed of a Blend of Ethylene–Vinyl Acetate Copolymer and Poly (d,l–lactic acid), *Cancer Letters*, 88 (1995) 73–79.

Leong, K.W., et al., Polymeric Controlled Drug Delivery, *Advanced Drug Delivery Reviews*, 1 (1987) 199–233.

Mao, Hai–Quan, et al., Synthesis and Biological Properties of Polymer Immunoadjuvants, *Polymer Journal*, vol. 25, No. 5, pp. 499–505 (1993).

Winternitz, Charles I., et al., Development of a Polymeric Surgical Paste Formulation for Taxol, *Pharmaceutical Research*, vol. 13, No. 3, pp. 368–375, 1996.

Wang, Ya Min, et al., Preparation and Characterization of Poly(lactic–co–glycolic acid) Microspheres for Targeted Delivery of a Novel Anticancer Agent, Taxol, *Chem. Pharm. Bull.* 44 (10) 1935–1940 (1996).

Sharma, Dayanand, Novel Taxol® Formulation: Polyvinylpyrrolidone Nanoparticle–Encapsulated Taxol® for Drug Delivery in Cancer Therapy, *Oncology Research*, vol. 8, Nos. 7/8, pp. 281–286, 1996.

Alkan–Onyuksel, Hayat, et al., A Mixed Micellar Formulation Suitable for the Parenteral Administration of Taxol, *Pharmaceutical Research*, vol. 11, No. 2, pp. 206–211, 1994.

Dordunoo, S.K., et al., Release of Taxol from Poly ($\epsilon$–caprolactone) Pastes: Effect of Water–Soluble Additives, *Journal of Controlled Release*, 44 (1997) 87–94.

Suh, Hearan, et al., Regulation of Smooth Muscle Cell Proliferation Using Paclitaxel–Loaded Poly(ethylene oxide)–poly(lactide/glycolide) Nanospheres, *J. Biomed. Mater. Res.* 42(2): 331–8 (1998).

Chemical Abstracts, vol. 99, No. 22, abstract No. 176481 Akutin et al. Polyarylates (1983).

Langer et al., "Chemical and Physical Structure of Polymers as Carriers for Controlled Release of Bioactive Agents", *J. Macro. Sci., Rev. Macro. Chem. Phys.*, C23(1), 61–125 (1983).

Chien, Y.W. et al., *Novel Drug Delivery Systems* (1982).

Pitt et al., "Biodegradable Drug Delivery Systems Based on Aliphatic Polyesters: Application to Contraceptives and Narcotic Antagonists", *Controlled Release of Bioactive Materials*, 19–44 (Richard Baker, ed., 1980).

Heller et al., "Release of Norethindrone form Poly(Ortho Esters)", *Polymer Engineering and Sci*, 21:11, 727–31 (1981).

Leong et al., "Polyanhydrides for Controlled Release of Bioactive Agents", *Biomaterials*, 7:364 (1986).

Kadiyala et al., *Biomedical Applications of Synthetic Biodegradable Polymers*, Chapter 3: "Poly(phosphoesters): Synthesis, Physicochemical Characterization and Biological Response", 33–57, (Jeffrey O. Hollinger ed., 1995).

Leong et al., "Polymeric Controlled Drug Delivery", *Advanced Drug Delivery Reviews*, 1:199–233 (1987).

Langer et al., "New Methods of Drug Delivery", *Science,* 249(4976):1527–33 (1990).

Pulapura et al., "Trends in the Development of Bioresorbable Polymers for Medical Applications", *Journal of Biomaterials Applications,* 6(1):216–50 (1992).

Bruin et al., "Biodegradable Lysine Diisocyanate–based Poly(glycolide–co–ε–caprolactone) –urethane Network in Artificial Skin", *Biomaterials,* 11(4):291–95 (1990).

Penczek et al., "Phosphorus–Containing Polymers", *Handbook of Polymer Synthesis,* Part B, Chpt. 17, 1077–1132 (Kricheldorf ed. 1992).

Pretula et al., "High–Molecular–Weight Poly(alkylene phosphonate)s by Condensation of Dialkylphosphonates with Diols", *Makromol. Chem.,* 119:671–80 (1990).

Hungnan Lo, "Synthesis of Biodegradable Polymers and Porous Grafts for Orthopedic Applications" (Jan. 27, 1995) (Ph.D. dissertation, The Johns Hopkins University).

BIODEGRADABLE TEREPHTHALATE POLYESTER-POLY (PHOSPHONATE) COMPOSITIONS, ARTICLES, AND METHODS OF USING THE SAME

BACKGROUND OF THE INVENTION

1. Field of the Invention

The present invention relates to biodegradable homopolymer and block copolymer compositions, in particular those containing both phosphonate and terephthalate ester linkages in the polymer backbone, which degrade in vivo into non-toxic residues. The copolymers of the invention are particularly useful as implantable medical devices and drug delivery systems.

2. Description of the Prior Art

Biocompatible polymeric materials have been used extensively in therapeutic drug delivery and medical implant device applications. Sometimes, it is also desirable for such polymers to be, not only bio-compatible, but also biodegradable to obviate the need for removing the polymer once its therapeutic value has been exhausted.

Conventional methods of drug delivery, such as frequent periodic dosing, are not ideal in many cases. For example, with highly toxic drugs, frequent conventional dosing can result in high initial drug levels at the time of dosing, often at near-toxic levels, followed by low drug levels between doses that can be below the level of their therapeutic value. However, with controlled drug delivery, drug levels can be more easily maintained at therapeutic, but non-toxic, levels by controlled release in a predictable manner over a longer term.

If a biodegradable medical device is intended for use as a drug delivery or other controlled-release system, using a polymeric carrier is one effective means to deliver the therapeutic agent locally and in a controlled fashion, see Langer et al., "Chemical and Physical Structures of Polymers as Carriers for Controlled Release of Bioactive Agents", *J. Macro. Science, Rev. Macro. Chem. Phys.*, C23:1, 61–126 (1983). As a result, less total drug is required, and toxic side effects can be minimized. Polymers have been used as carriers of therapeutic agents to effect a localized and sustained release. See Leong et al., "Polymeric Controlled Drug Delivery", *Advanced Drug Delivery Reviews*, 1:199–233 (1987) and Langer, "New Methods of Drug Delivery", *Science*, 249:1527–33 (1990); and Chien et al., *Novel Drug Delivery Systems* (1982). Such delivery systems offer the potential of enhanced therapeutic efficacy and reduced overall toxicity.

For a non-biodegradable matrix, the steps leading to release of the therapeutic agent are water diffusion into the matrix, dissolution of the therapeutic agent, and diffusion of the therapeutic agent out through the channels of the matrix. As a consequence, the mean residence time of the therapeutic agent existing in the soluble state is longer for a non-biodegradable matrix than for a biodegradable matrix, for which passage through the channels of the matrix, while it may occur, is no longer required. Since many pharmaceuticals have short half-lives, therapeutic agents can decompose or become inactivated within the non-biodegradable matrix before they are released.

This issue is particularly significant for many bio-macromolecules and smaller polypeptides, since these molecules are generally hydrolytically unstable and have low permeability through a polymer matrix. In fact, in a non-biodegradable matrix, many bio-macromolecules aggregate and precipitate, blocking the channels necessary for diffusion out of the carrier matrix.

These problems are alleviated by using a biodegradable matrix that, in addition to some diffusion release, also allows controlled release of the therapeutic agent by degradation of the polymer matrix. Examples of classes of synthetic polymers that have been studied as possible biodegradable materials include polyesters (Pitt et al., "Biodegradable Drug Delivery Systems Based on Alipathic Polyesters: Application to Contraceptives and Narcotic Antagonists", *Controlled Release of Bioactive Materials*, 19–44 (Richard Baker ed., 1980); poly(amino acids) and pseudo-poly(amino acids) (Pulapura et al., "Trends in the Development of Bioresorbable Polymers for Medical Applications," *J. of Biomaterials Appl.*, 6:1, 216–50 (1992); polyurethanes (Bruin et al., "Biodegradable Lysine Diisocyanate-based Poly-(Glycolide-co-ε Caprolactone)-Urethane Network in Artificial Skin", *Biomaterials*, 11:4, 291–95 (1990); poly-orthoesters (Heller et al., "Release of Norethindrone from Poly(ortho Esters)", *Polymer Engineering Sci.*, 21:11, 727–31 (1981); and polyanhydrides (Leong et al., "Polyanhydrides for Controlled Release of Bioactive Agents", *Biomaterials*, 7:5, 364–71 (1986).

Specific examples of biodegradable materials that are used as medical implant materials are polylactide, polyglycolide, polydioxanone, poly(lactide-co-glycolide), poly(glycolide-co-polydioxanone), polyanhydrides, poly(glycolide-co-trimethylene carbonate), and poly(glycolide-co-caprolactone). Injectable polyphosphazenes have also been described as useful for forming solid biodegradable implants in situ. See, Dunn et al., in U.S. Pat. Nos. 5,340,849; 5,324,519; 5,278,202; and 5,278,201.

Polymers having phosphoester linkages, called poly(phosphates), poly(phosphonates) and poly(phosphites), are known. See Penczek et al., *Handbook of Polymer Synthesis*, Chapter 17: "Phosphorus-Containing Polymers", 1077–1132 (Hans R. Kricheldorf ed., 1992). The respective structures of each of these three classes of compounds, each having a different side chain connected to the phosphorus atom, is as follows:

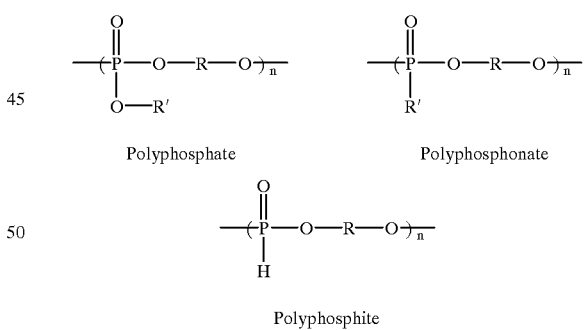

Polyphosphate    Polyphosphonate

Polyphosphite

The versatility of these polymers comes from the versatility of the phosphorus atom, which is known for a multiplicity of reactions. Its bonding can involve the 3p orbitals or various 3s–3p hybrids; spd hybrids are also possible because of the accessible d orbitals. Thus, the physico-chemical properties of the poly(phosphoesters) can be readily changed by varying either the R or R' group. The biodegradability of the polymer is due primarily to the physiologically labile phosphoester bond in the backbone of the polymer. By manipulating the backbone or the side chain, a wide range of biodegradation rates are attainable. Kadiyala et al., *Biomedical Applications of Synthetic Bio-*

*degradable Polymers,* Chapter 3: "Poly(phosphoesters): Synthesis, Physicochemical Characterization and Biological Response", 33–57, 34–5 (Jeffrey O. Hollinger ed., 1995).

An additional feature of poly(phosphoesters) is the availability of functional side groups. Because phosphorus can be pentavalent, drug molecules or other biologically active substances can be chemically linked to the polymer. For example, drugs with —O- carboxy groups may be coupled to the phosphorus via an ester bond, which is hydrolyzable. The P—O—C group in the backbone also lowers the glass transition temperature of the polymer and, importantly, confers solubility in common organic solvents, which is desirable for easy characterization and processing. Kadiyala et al. at page 35.

Specifically, EP 386 757 discloses the use of poly (phosphate) esters as prostheses and therapeutic agent delivery vehicles, recognizing that the polymers are biodegradable because of the hydrolyzable phosphoester bond in the backbone. With phosphorous in the trivalent state, the polymers can be polyphosphates or polyphosphonates having the general formula:

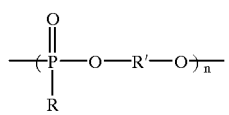

where R and R are organic or organometallic moieties, and n is from about 10 to about $10^5$.

Similarly, EP 057 116 discloses biocompatible polyphosphate esters with difunctional oligomers joined by phosphate bridging structures of general formula I:

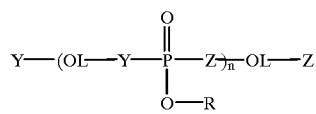

where $n \geq 2$; OL is an oligomer, preferably chosen from the group compring polyethylene terephthalate and polybutylene terephthalate; Y and Z are the two functional groups of the oligomer, such as OH; and R can be a substituted or unsubstituted alkyl, aryl or aralkyl group. These compounds are described as allowing for easy adjustment of the biodegradability.

Kadiyala et al. specifically discloses reacting bis(2-hydroxyethyl) terephthalate with dimethyl phosphite to form the following biodegradable poly-(phosphite)

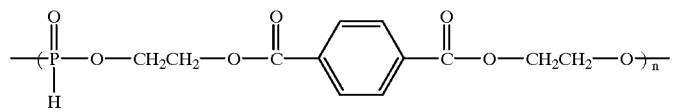

The corresponding terephthalate poly(phosphate) materials have been described as biodegradable materials in copending U.S. patent application Ser. No. 09/053,648 filed Apr. 2, 1998.

Login et al., in U.S. Pat. Nos. 4,259,222; 4,315,847; and 4,315,969, disclose a poly(phosphate)-polyester polymer having a halogenated terephthalate recurring unit useful in flame retardant materials, but without a phosphorus having a side chain.

A number of other U.S. patents disclose poly-(phosphonate) compounds that are useful for their flame retardant qualities, such as Ko et al., U.S. Pat. No. 5,399,654; Besecke et al., U.S. Pat. Nos. 4,463,159 and 4,472,570; Login et al., U.S. Pat. Nos. 4,259,222, 4,315,847, and 4,315,969; Okamato et al., U.S. Pat. Nos. 4,072,658 and 4,156,663; Schmidt et al., U.S. Pat. Nos. 4,328,174 and 4,374,971; and Hechenbleikner, U.S. Pat. No. 4,082,897, or for their soil release effects, such as Engelhardt et al., U.S. Pat. No. 5,530,093. Certain terephthalate poly(phosphonate) compounds are disclosed as flame retardants by Desitter et al., U.S. Pat. No. 3,927,231; Reader, U.S. Pat. No. 3,932,566; and Starck et al., Canadian Patent No. 597,473. However, there still remains a need for further materials that are particularly well-suited for making biodegradable medical devices and drug delivery systems.

SUMMARY OF THE INVENTION

Applicants now have discovered that medical devices can be advantageously be made of a composition comprising biodegradable terephthalate polymers comprising the recurring monomeric units shown in formula I:

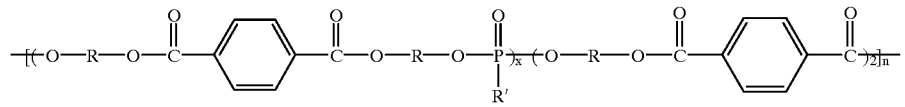

wherein R is a divalent organic moiety;

R' is an aliphatic, aromatic or heterocyclic residue;

x is $\geq 1$; and n is 3–7,500, where the biodegradable polymer is sufficiently pure to be biocompatible and is capable of forming biocompatible residues upon biodegradation. Preferably, the device of the invention is adapted for implantation or injection into the body of an animal.

In another embodiment, the invention comprises polymer compositions comprising:

(a) at least one biologically active substance and (b) a polymer having the recurring monomeric units shown above in formula I.

In a still further embodiment of the invention, a method is provided for the controlled release of a biologically active substance comprising the steps of:

(a) combining the biologically active substance with a biodegradable terephthalate polymer having the recurring monomeric units shown in formula I to form an admixture;

(b) forming the admixture into a shaped, solid article; and (c) implanting or injecting the solid article in vivo at a preselected site, such that the solid, implanted or injected article is in at least partial contact with a biological fluid.

DETAILED DESCRIPTION OF THE INVENTION

Polymers of the Invention

Figure 1:
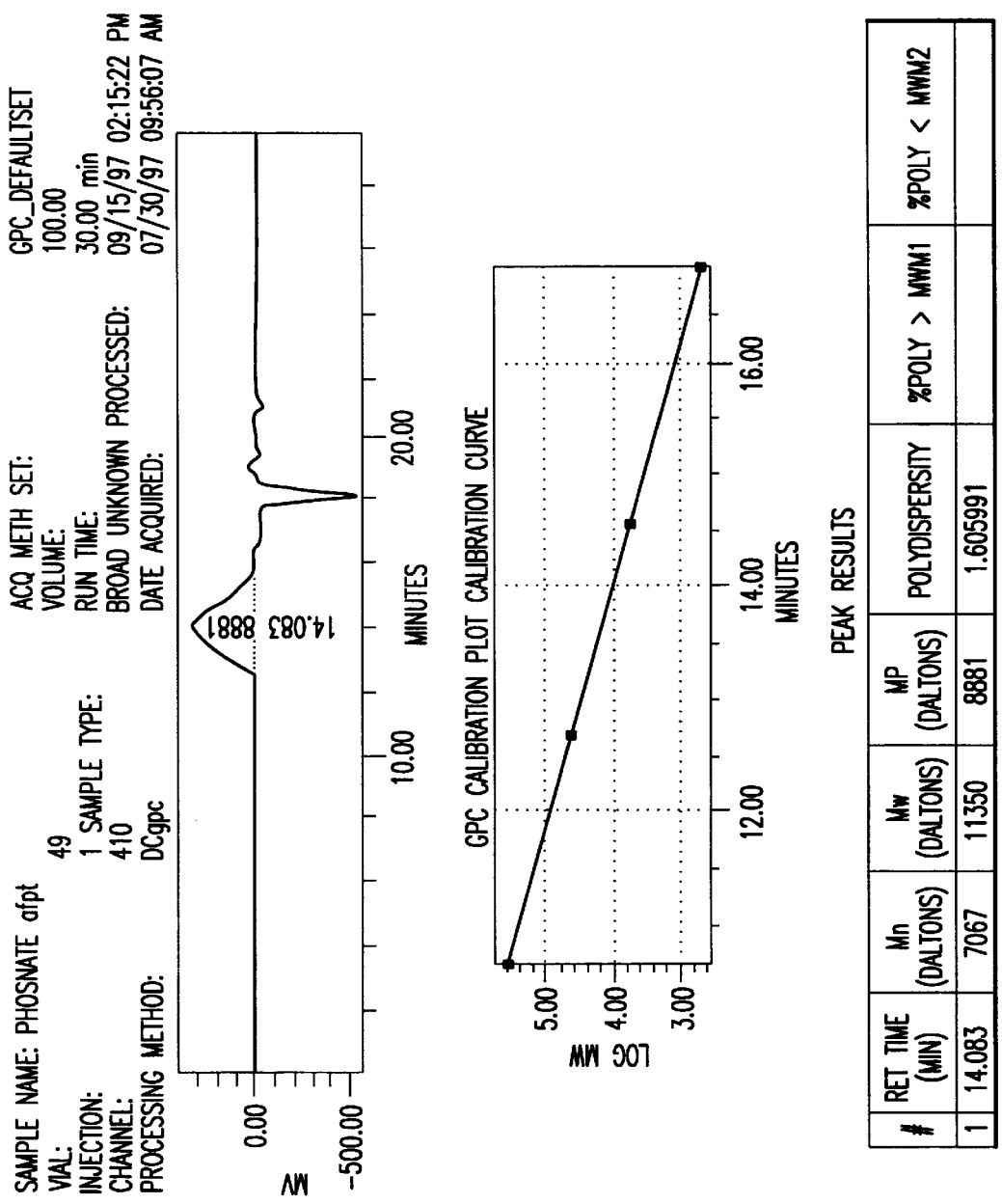
FIG. 1 shows a GPC chromatogram for poly(BHET-EP) prepared in Example 2.

As used herein, the term "aliphatic" refers to a linear, branched, or cyclic alkane, alkene, or alkyne. Preferred aliphatic groups in the poly(phosphonate) polymer of the invention are linear or branched alkanes having from 1 to 10 carbons, preferably being linear alkane groups of 1 to 7 carbon atoms.

As used herein, the term "aromatic" refers to an unsaturated cyclic carbon compound with 4n+2 π electrons.

As used herein, the term "heterocyclic" refers to a saturated or unsaturated ring compound having one or more atoms other than carbon in the ring, for example, nitrogen, oxygen or sulfur.

The medical device comprising the biodegradable terephthalate block copolymer composition of the invention comprises the recurring monomeric units shown in formula I:

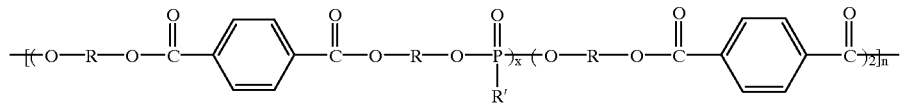

wherein R is a divalent organic moiety. R can be any divalent organic moiety so long as it does not interfere with the polymerization, copolymerization, or biodegradation reactions of the copolymer. Specifically, R can be an aliphatic group, for example, alkylene, such as ethylene, 1,2-dimethylethylene, n-propylene, isopropylene, 2-methylpropylene, 2,2-dimethylpropylene or tert-butylene, tertpentylene, n-hexylene, n-heptylene and the like; alkenylene, such as ethenylene, propenylene, dodecenylene, and the like; alkynylene, such as propynylene, hexynylene, octadecynylene, and the like; an aliphatic group substituted with a non-interfering substituent, for example, hydroxy-, halogen- or nitrogen-substituted aliphatic group; or a cycloaliphatic group such as cyclopentylene, 2-methylcyclopentylene, cyclohexylene, cyclohexenylene and the like.

R can also be a divalent aromatic group, such as phenylene, benzylene, naphthalene, phenanthrenylene, and the like, or a divalent aromatic group substituted with a non-interfering substituent. Further, R can also be a divalent heterocyclic group, such as pyrrolylene, furanylene, thiophenylene, alkylene-pyrrolylene-alkylene, pyridylene, pyridinylene, pyrimidinylene and the like, or may be any of these substituted with a non-interfering substituent.

Preferably, however, R is an alkylene group, a cycloaliphatic group, a phenylene group, or a divalent group having the formula:

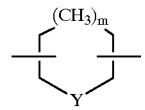

wherein Y is oxygen, nitrogen, or sulfur, and m is 1 to 3. More preferably, R is an alkylene group having from 1 to 7 carbon atoms and, most preferably, R is an ethylene group.

R' in the polymer of the invention is an aliphatic, aromatic or heterocyclic residue. When R' is aliphatic, it is preferably alkyl, such as methyl, ethyl, n-propyl, i-propyl, n-butyl, tert-butyl, —$C_8H_{17}$, and the like; or alkyl substituted with a non-interfering substituent, such as halogen, alkoxy or nitro.

When R' is aromatic, it typically contains from about 5 to about 14 carbon atoms, preferably about 5 to 12 carbon atoms and, optionally, can contain one or more rings that are fused to each other. Examples of particularly suitable aromatic groups include phenyl, naphthyl, anthracenyl, phenanthrenyl and the like.

When R' is heterocyclic, it typically contains from about 5 to 14 ring atoms, preferably from about 5 to 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando-[3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 1,2-benzo-diazine, 1,3-benzodiazine, naphthyridine, pyrido-[3,4-b]pyridine, pyrido[3,2-b]-pyridine, pyrido-[4,3-b] pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. Preferably, when R' is heterocyclic, it is selected from the group consisting of furan, pyridine, N-alkyl-pyridine, 1,2,3- and 1,2,4-triazoles, indene, anthracene and purine.

In a particularly preferred embodiment, R' is an alkyl group or a phenyl group and, even more preferably, an alkyl group having from 1 to 7 carbon atoms. Most preferably, R' is an ethyl group.

The value of x can vary depending on the desired solubility of the polymer, the desired Tg, the desired stability of the polymer, the desired stiffness of the final polymers, and the biodegradability and the release characteristics desired in the polymer. However, x generally is $\geq 1$ and, typically, varies between 1 and 40. Preferably, x is from about 1 to about 30, more preferably, from about 1 to about 20 and, most preferably, from about 2 to about 20.

The most common way of controlling the value of x is to vary the feed ratio of the "x" portion relative to the monomer. For example, in the case of making the polymer:

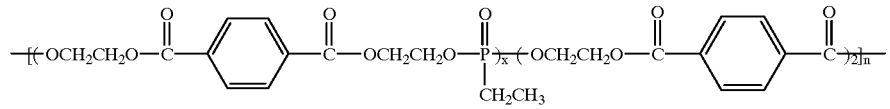

widely varying feed ratios of the ethyl phosphonic dichloride "x" reactant ("EP") can be used with the terephthaloyl chloride reactant ("TC"). Feed ratios of EP to TC can easily vary from 99:1 to 1:99, for example, 95:5, 90:10, 85:15, 80:20, 75:25, 70:30, 65:35, 60:40, 55:45, 50:50, 45:55, 20:80, 15:85, and the like. Preferably, the feed ratio between the phosphonic dichloride reactant and the TC reactant varies from about 90:10 to about 50:50; even more preferably, from about 85:15 to about 50:50; and most preferably, from about 80:20 to about 50:50.

The number n can vary greatly depending on the biodegradability and the release characteristics desired in the polymer, but typically varies from about 3 to 7,500, preferably between 5 and 5,000. More preferably, n is from about 5 to about 300 and most preferably, from about 5 to about 200.

The polymer of the invention can also comprise additional biocompatible monomeric units so long as they do not interfere with the biodegradable characteristics desired. Such additional monomeric units may offer even greater flexibility in designing the precise release profile desired for targeted drug delivery or the precise rate of biodegradability desired for structural implants such as for orthopedic applications. Examples of such additional biocompatible monomers include the recurring units found in polycarbonates; polyorthoesters; polyamides; polyurethanes; poly(iminocarbonates); and polyanhydrides.

Biodegradable polymers differ from non-biodegradable polymers in that they can be degraded during in vivo therapy. This generally involves breaking down the polymer into its monomeric subunits. In principle, the ultimate hydrolytic breakdown products of a poly(phosphonate) are phosphonate, alcohol, and diol, all of which are potentially non-toxic. The intermediate oligomeric products of the hydrolysis may have different properties, but the toxicology of a biodegradable polymer intended for implantation or injection, even one synthesized from apparently innocuous monomeric structures, is typically determined after one or more in vitro toxicity analyses.

The biodegradable polymer composition of the invention is preferably sufficiently pure to be biocompatible itself and remains biocompatible upon biodegradation. By "biocompatible" is meant that the biodegradation products or the polymer are non-toxic and result in only minimal tissue irritation when implanted or injected into vasculated tissue.

The polymer of the invention is preferably soluble in one or more common organic solvents for ease of fabrication and processing. Common organic solvents include such solvents as chloroform, dichloromethane, acetone, ethyl acetate, DMAC, N-methyl pyrrolidone, dimethylformamide, and dimethylsulfoxide. The polymer is preferably soluble in at least one of the above solvents.

The glass transition temperature (Tg) of the polymer of the invention can vary widely depending upon the branching of the diols used to prepare the polymer, the relative proportion of phosphorus-containing monomer used to make the polymer, and the like. However, preferably, the Tg is within the range of about $-10°$ C. to about $100°$ C. and, even more preferably, between about 0 and $50°$ C.

Synthesis of Polyester-Poly(phosphonate) Polymers

The most common general reaction in preparing a poly(phosphonate) is a dehydrochlorination between a phosphonic dichloride and a diol according to the following equation:

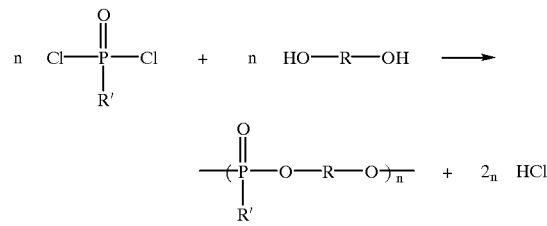

A Friedel-Crafts reaction can also be used to synthesize poly(phosphonates). Polymerization typically is effected by reacting either bis(chloromethyl) compounds with aromatic hydrocarbons or chloromethylated diphenyl ether with triaryl phosphonates. Poly(phosphonates) can also be obtained by bulk condensation between phosphorus diimidazolides and aromatic diols, such as resorcinol and quinoline, usually under nitrogen or some other inert gas.

An advantage of bulk polycondensation is that it avoids the use of solvents and large amounts of other additives, thus making purification more straightforward. It can also provide polymers of reasonably high molecular weight. Somewhat rigorous conditions, however, are often required and can lead to chain acidolysis (or hydrolysis if water is present). Unwanted, thermally-induced side reactions, such as cross-linking reactions, can also occur if the polymer backbone is susceptible to hydrogen atom abstraction or oxidation with subsequent macroradical recombination. To minimize these side reactions, the polymerization is preferably carried out in solution.

Solution polycondensation requires that both the diol and the phosphorus component be soluble in a common solvent. Typically, a chlorinated organic solvent is used, such as chloroform, dichloromethane, or dichloroethane. The solution polymerization is preferably run in the presence of equimolar amounts of the reactants and a stoichiometric amount of an acid acceptor, usually a tertiary amine such as pyridine or triethylamine. The product is then typically isolated from the solution by precipitation with a non-solvent and purified to remove the hydrochloride salt by conventional techniques known to those of ordinary skill in the art, such as by washing with an aqueous acidic solution, e.g., dilute HCl.

Reaction times tend to be longer with solution polymerization than with bulk polymerization. However, because overall milder reaction conditions can be used, side reactions are minimized, and more sensitive functional groups can be incorporated into the polymer. The disadvantages of solution polymerization are that the attainment of high molecular weights, such as a Mw greater than 20,000, is less likely.

Interfacial polycondensation can be used when high molecular weight polymers are desired at high reaction rates. Mild conditions minimize side reactions. Also the dependence of high molecular weight on stoichiometric equivalence between diol and dichloride inherent in solution methods is removed. However, hydrolysis of the acid chloride may occur in the alkaline aqueous phase. Sensitive dichlorides that have some solubility in water are generally subject to hydrolysis rather than polymerization. Phase transfer catalysts, such as crown ethers or tertiary ammonium chloride, can be used to bring the ionized diol to the interface to facilitate the polycondensation reaction. The yield and molecular weight of the resulting polymer after interfacial polycondensation are affected by reaction time, molar ratio of the monomers, volume ratio of the immiscible solvents, the type of acid acceptor, and the type and concentration of the phase transfer catalyst.

In a preferred embodiment of the invention, the biodegradable terephthalate polymer of formula I comprises the steps of polymerizing p moles of a diol compound having formula II:

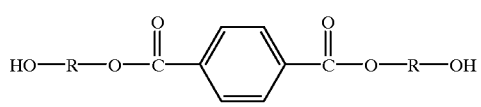

II wherein R is as defined above, with q moles of a phosphonic dichloride of formula III:

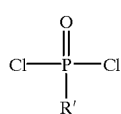

III wherein R' is defined as above, and p>q, to form q moles of a homopolymer of formula IV, shown below:

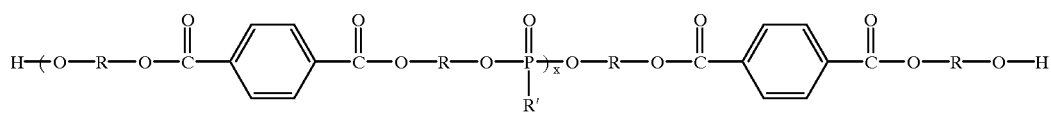

IV wherein R, R' and x are as defined above. The homopolymer so formed can be isolated, purified and used as is. Alternatively, the homopolymer, isolated or not, can be used to prepare a block copolymer composition of the invention by:

(a) polymerizing as described above; and (b) further reacting the homopolymer of formula IV and excess diol of formula II with (p–q) moles of terephthaloyl chloride having the formula V:

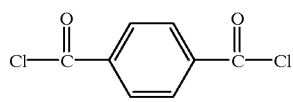

V to form the copolymer of formula I.

The function of the polymerization reaction of step (a) is to phosphorylate the di-ester starting material and then to polymerize it to form the homopolymer. The polymerization step (a) can take place at widely varying temperatures, depending upon the solvent used, the solubility desired, the molecular weight desired and the susceptibility of the reactants to form side reactions. Preferably, however, the polymerization step (a) takes place at a temperature from about −40 to about +160° C. for solution polymerization, preferably from about 0 to 65° C.; in bulk, temperatures in the range of about +150° C. are generally used.

The time required for the polymerization step (a) also can vary widely, depending on the type of polymerization being used and the molecular weight desired. Preferably, however, the polymerization step (a) takes place during a time between about 30 minutes and 24 hours.

While the polymerization step (a) may be in bulk, in solution, by interfacial polycondensation, or any other convenient method of polymerization, preferably, the polymerization step (a) is a solution polymerization reaction. Particularly when solution polymerization reaction is used, an acid acceptor is advantageously present during the polymerization step (a). A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethylaminopyridine ("DMAP").

The addition sequence for the polymerization step (a) can vary significantly depending upon the relative reactivities of the diol of formula II, the phosphonic dichloride of formula III, and the homopolymer of formula IV; the purity of these reactants; the temperature at which the polymerization reaction is performed; the degree of agitation used in the polymerization reaction; and the like. Preferably, however, the diol of formula II is combined with a solvent and an acid acceptor, and then the phosphonic dichloride is added slowly. for example, a solution of the phosphonic dichloride in a solvent may be trickled in or added dropwise to the chilled reaction mixture of diol, solvent and acid acceptor, to control the rate of the polymerization reaction.

The purpose of the copolymerization of step (b) is to form a block copolymer comprising (i) the phosphorylated homopolymer chains produced as a result of polymerization step (a) and (ii) interconnecting polyester units. The result is a block copolymer having a microcrystalline structure particularly well-suited to use as a controlled release medium.

The copolymerization step (b) of the invention usually takes place at a slightly higher temperature than the temperature of the polymerization step (a), but also may vary widely, depending upon the type of copolymerization reaction used, the presence of one or more catalysts, the molecular weight desired, the solubility desired, and the susceptibility of the reactants to undesirable side reaction. However, when the copolymerization step (b) is carried out as a solution polymerization reaction, it typically takes place at a temperature between about −40 and 100° C. Typical solvents include methylene chloride, chloroform, or any of a wide variety of inert organic solvents.

The time required for the copolymerization of step (b) can also vary widely, depending on the molecular weight of the material desired and, in general, the need to use more or less rigorous conditions for the reaction to proceed to the desired degree of completion. Typically, however, the copolymerization step (b) takes place during a time of about 30 minutes to 24 hours.

The time required for the copolymerization of step (b) can also vary widely, depending on the molecular weight of the material desired and, in general, the need to use more or less rigorous conditions for the reaction to proceed to the desired degree of completion. Typically, however, the copolymerization step (b) takes place during a time of about 30 minutes to 24 hours.

When the polymer of the invention is synthesized by a two-step solution polycondensation to produce a block copolymer, the addition sequence of the reactive chlorides and the reaction temperatures in each step are preferably optimized to obtain the combination of molecular weight desired with good solubility in common organic solvents. Preferably, the additive sequence comprises dissolving the bisterephthalate starting material with an acid acceptor in a solvent in which both are soluble, chilling the solution with stirring, slowly adding an equal molar amount of the phosphonic dichloride (dissolved in the same solvent) to the solution, allowing the reaction to proceed at room temperature for a period of time, slowly adding an appropriate amount of terephthaloyl chloride, which is also dissolved in the same solvent, and increasing the temperature to about 50° C. before refluxing overnight.

The polymer of formula I, whether a homopolymer or a block polymer, is isolated from the reaction mixture by conventional techniques, such as by precipitating out, extraction with an immiscible solvent, evaporation, filtration, crystallization and the like. Typically, however, the polymer of formula I is both isolated and purified by quenching a solution of said polymer with a non-solvent or a partial solvent, such as diethyl ether or petroleum ether.

Biodegradability and Release Characteristics

The polymer of formula I is usually characterized by a release rate of the biologically active substance in vivo that is controlled at least in part as a function of hydrolysis of the phosphoester bond of the polymer during biodegradation.

Further, the structure of the side chain can influence the release behavior of the polymer. For example, it is expected that conversion of the phosphorus side chain to a more lipophilic, more hydrophobic or bulky group would slow down the degradation process. Thus, for example, release is usually faster from copolymer compositions with a small aliphatic group side chain than with a bulky aromatic side chain.

The lifetime of a biodegradable polymer in vivo also depends upon its molecular weight, crystallinity, biostability, and the degree of cross-linking. In general, the greater the molecular weight, the higher the degree of crystallinity, and the greater the biostability, the slower biodegradation will be.

Polymer Compositions

The polymer of formula I is preferably used as a composition containing, in addition to the polymer, a biologically active substance to form a variety of useful biodegradable materials. However, the polymer of formula I can be used as a medical device in the form of a biosorbable suture, an orthopedic appliance or bone cement for repairing injuries to bone or connective tissue, a laminate for degradable or non-degradable fabrics, or a coating for an implantable device, even without the presence of a biologically iactive substance.

Preferably, the biodegradable terephthalate polymer composition comprises both:

(a) at least one biologically active substance and (b) the copolymer having the recurring monomeric units shown in formula I where R, R', x and n are as defined above.

The biologically active substance of the invention can vary widely with the purpose for the composition. The active substance(s) may be described as a single entity or a combination of entities. The delivery system is designed to be used with biologically active substances having high water-solubility as well as with those having low water-solubility to produce a delivery system that has controlled release rates. The term "biologically active substance" includes, without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of broad categories of useful biologically active substances include the following expanded therapeutic categories: anabolic agents, antacids, anti-asthmatic agents, anticholes-terolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and pro-drugs.

Specific examples of useful biologically active substances from the above categories include: (a) anti-neoplastics such as androgen inhibitors, anti-metabolites, cytotoxic agents, and immuno-modulators; (b) anti-tussives such as dextromethorphan, dextro-methorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) antiarrhythmics such as N-acetylprocainamide; (i) antipyretics and analgesics such as acetaminophen, aspirin and ibuprofen; (j) appetite suppressants such as phenylpropanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; and (n) anti-infective agents such as antifungals, antivirals, antiseptics and antibiotics.

Non-limiting examples of useful biologically active substances include the following therapeutic categories: Analgesics, such as nonsteroidal anti-inflammatory drugs, opiate agonists and salicylates; antihistamines, such as $H_1$-blockers and $H_2$-blockers; anti-infective agents, such as anthelmintics, anti-anaerobics, antibiotics, aminoglycoside antibiotics, antifungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, β-blocker sympatholytics, sympathomimetics, and adrenergic agonist sympathomimetics; cardiovascular agents, such as antianginals, β-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, α-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic anti-hypertensive agents, peripheral vasodilator anti-hypertensives, anti-lipemics, bile acid sequestrant anti-lipemics, HMG-CoA reductase inhibitor anti-lipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as anti-diarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and pro-kinetic agents; general anesthetics, such as inhalation anesthetics, halogenated inhalation anesthetics, intravenous anesthetics, barbiturate intravenous anesthetics, benzodiaz- epine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and toco-lytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzo-diazepine anticonvulsants, anti-migraine agents, anti-parkinsonian agents, anti-vertigo agents, opiate agonists, and opiate antagonists; ophthalmic agents, such as anti-glaucoma agents, β-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic anti-depressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Preferred classes of useful biologically active substances from the above categories include: (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) $H_1$-blocker antihistamines, such as clemastine and terfenadine; (5) $H_2$-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous β-lac-tam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) anti-protozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alfa, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alfa, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasym-pathomimetics, such as pilocarpine; (32) cholinesterase inhibitor parasympathomimetics, such as pyridostigmine; (33) α-blocker sympatholytics, such as prazosin; (34) β-blocker sympatholytics, such as atenolol; (35) adrenergic agonist sympathomimetics, such as albuterol and dobutamine; (36) cardiovascular agents, such as aspirin (ASA) (enteric coated ASA); (37) β-blocker antianginals, such as atenolol and propranolol; (38) calcium-channel blocker anti-anginals, such as nifedipine and verapamil; (39) nitrate antianginals, such as isosorbide dinitrate (ISDN); (40) cardiac glycoside antiarrhythmics, such as digoxin; (41) class I antiarrhythmics, such as lidocaine, mexiletine, phenytoin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) α-blocker antihypertensives, such as prazosin; (46) angiotensin-converting enzyme inhibitor (ACE inhibitor) antihypertensives, such as captopril and enalapril; (47) β-blocker antihypertensives, such as atenolol, metoprolol, nadolol, and propanolol; (48) calcium-channel blocker antihypertensive agents, such as diltiazem and nifedipine; (49) central-acting adrenergic antihyper-tensives, such as clonidine and methyldopa; (50) diuretic antihypertensive agents, such as amiloride, furosemide, hydrochlorothiazide (HCTZ), and spironolactone; (51) peripheral vasodilator antihypertensives, such as hydralazine and minoxidil; (52) anti-lipemics, such as gemfibrozil and probucol; (53) bile acid sequestrant anti-lipemics, such as cholestyramine; (54) HMG-COA reductase inhibitor anti-lipemics, such as lovastatin and pravastatin; (55) inotropes, such as amrinone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) anti-fungal topical anti-infectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic anti-anemia agents, such as erythro-poietin, filgrastim (G-CSF), and sargramostim (GM-CSF); (78) coagulation agents, such as antihemophilic factors 1–10 (AHF 1–10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) anti-diabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-parkinsonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) β-blocker anti-glaucoma agents, such as timolol; (110) miotic anti-glaucoma agents, such as pilocarpine; (111) ophthalmic aminoglycoside anti-infectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psycho-stimulants, such as methylphenidate and pemoline; (118) antitussives, such as codeine; (119) bronchodilators, such as theophylline; (120) adrenergic agonist broncho-dilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyano-cobalamin (vitamin $B_{12}$) and niacin (vitamin $B_3$); (128) vitamin C compounds, such as ascorbic acid; and (129) vitamin D compounds, such as calcitriol.

In addition to the foregoing, the following less common drugs may also be used: Chlorhexidine, estradiol cypionate in oil, estradiol valerate in oil, flurbiprofen, flurbiprofen sodium, ivermectin, levodopa, nafarelin, and somatropin.

Further, the following new drugs may also be used: Recombinant beta-glucan; bovine immunoglobulin concentrate; bovine superoxide dismutase; a mixture comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan.

Further still, the following intravenous products may be used: acyclovir sodium, aldesleukin, atenolol, bleomycin sulfate, human calcitonin, salmon calcitonin, carboplatin, carmustine, dactinomycin, daunorubicin HCl, docetaxel, doxorubicin HCl, epoetin alfa, etoposide (VP-16), fluorouracil (5-FU), ganciclovir sodium, gentamicin sulfate, interferon alfa, leuprolide acetate, meperidine HCl, methadone HCl, methotrexate sodium, paclitaxel, ranitidine HCl, vinblastin sulfate, and zidovudine (AZT).

Still further, the following listing of peptides, proteins, and other large molecules may also be used, such as interleukins 1 through 18, including mutants and analogues; interferons α, β, and γ; luteinizing hormone releasing hormone (LHRH) and analogues, gonadotropin releasing hormone (GnRH), and transforming growth factor-β (TGF-β); fibroblast growth factor (FGF); tumor necrosis factor-α & β (TNF-α & β); nerve growth factor (NGF); growth hormone releasing factor (GHRF); epidermal growth factor (EGF); fibroblast growth factor homologous factor (FGFHF); hepatocyte growth factor (HGF); insulin growth factor (IGF); invasion inhibiting factor-2 (IIF-2); bone morphogenetic proteins 1–7 (BMP 1–7); somatostatin; thymosin-α-1; γ-globulin; superoxide dismutase (SOD); and complement factors.

Preferably, the biologically active substance is selected from the group consisting of peptides, polypeptides, proteins, amino acids, polysaccharides, growth factors, hormones, anti-angiogenesis factors, interferons or cytokines, and pro-drugs. In a particularly preferred embodiment, the biologically active substance is a therapeutic drug or pro-drug, most preferably a drug selected from the group consisting of chemotherapeutic agents and other antineoplastics (such as paclitaxel), antibiotics, antivirals, antifungals, anti-inflammatories, anticoagulants, and pro-drugs of these substances.

The biologically active substances are used in amounts that are therapeutically effective. While the effective amount of a biologically active substance will depend on the particular material being used, amounts of the biologically active substance from about 1% to about 65% have been easily incorporated into the present delivery systems while achieving controlled release. Lesser amounts may be used to achieve efficacious levels of treatment for certain biologically active substances.

Pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition.

Implants and Delivery Systems Designed for Injection

In its simplest form, a biodegradable therapeutic agent delivery system consists of a dispersion of the therapeutic agent in a polymer matrix. The therapeutic agent is typically released as the polymeric matrix biodegrades in vivo into soluble products that can be absorbed by and eventually excreted from the body.

In a particularly preferred embodiment, an article is used for implantation, injection, or otherwise placed totally or partially within the body, the article comprising the biodegradable terephthalate polymer composition of the invention. The biologically active substance of the composition and the polymer of the invention may form a homogeneous matrix, or the biologically active substance may be encapsulated in some way within the polymer. For example, the biologically active substance may be first encapsulated in a microsphere and then combined with the polymer in such a way that at least a portion of the microsphere structure is maintained.

Alternatively, the biologically active substance may be sufficiently immiscible in the polymer of the invention that it is dispersed as small droplets, rather than being dissolved, in the polymer. Either form is acceptable, but it is preferred that, regardless of the homogeneity of the composition, the release rate of the biologically active substance in vivo remain controlled, at least partially as a function of hydrolysis of the phosphoester bond of the polymer upon biodegradation.

In a preferred embodiment, the article of the invention is adapted for implantation or injection into the body of an animal. It is particularly important that such an article result in minimal tissue irritation when implanted or injected into vasculated tissue.

As a structural medical device, the copolymer compositions of the invention provide a physical form having specific chemical, physical, and mechanical properties sufficient for the application and a composition that degrades in vivo into non-toxic residues. Typical structural medical articles include such implants as orthopedic fixation devices, ventricular shunts, laminates for degradable or nondegradable fabrics, drug-carriers, biosorbable sutures, burn dressings, coatings to be placed on other implant devices, and the like.

In orthopedic appliances, the composition of the invention may be a bone wax, bone cement or other material useful for repairing bone and connective tissue injuries. For example, a bio-degradable porous material can be loaded with bone morphogenetic proteins to form a bone graft useful for even large segmental defects. In vascular graft applications, a biodegradable material in the form of woven fabric can be used to promote tissue ingrowth. The copolymer composition of the invention may be used as a temporary barrier for preventing tissue adhesion, e.g., following abdominal surgery.

On the other hand, in nerve regeneration articles, the presence of a biodegradable supporting matrix can be used to facilitate cell adhesion and proliferation. When the copolymer composition is fabricated as a tube for nerve generation, for example, the tubular article can also serve as a geometric guide for axonal elongation in the direction of functional recovery.

As a drug delivery device, the copolymer composition of the invention provides a polymeric matrix capable of sequestering a biologically active substance and provides predictable, controlled delivery of the substance. The polymeric matrix then degrades to non-toxic residues.

Biodegradable medical implant devices and drug delivery products can be prepared in several ways. The copolymer can be melt processed using conventional extrusion or injection molding techniques, or these products can be prepared by dissolving in an appropriate solvent, followed by formation of the device, and subsequent removal of the solvent by evaporation or extraction. By these methods, the polymers may be formed into drug delivery systems of almost any size or shape desired, for example, implantable solid discs or wafers or injectable rods, microspheres, or other microparticles.

Once a medical implant article is in place, it should remain in at least partial contact with a biological fluid, such as blood, internal organ secretions, mucous membranes, cerebrospinal fluid and the like.

The following examples are illustrative of preferred embodiments of the invention and are not to be construed as limiting the invention thereto. All polymer molecular weights are average molecular weights. All percentages are based on the percent by weight of the final delivery system or formulation being prepared, unless otherwise indicated, and all totals equal 100% by weight.

EXAMPLES

Example 1

Preparation of Bis(2-hydroxyethyl)terephthalate

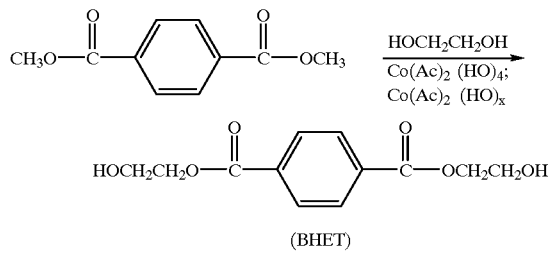

(BHET)

1.4 moles of dimethyl terephthalate (277 g) and 7.2 moles of ethylene glycol (445 g) were weighed into a one-liter round-bottomed flask connected to a vacuum line. A catalytic amount of cobalt (II) acetate tetrahydrate (180 mg, 0.5 mole) and calcium acetate hydrate (90 mg, 0.4 mole) were added. The reaction mixture was heated at 160° C. in an oil bath under a mild vacuum.

After 18 hours, the reaction was terminated. While still molten, the mixture was poured into cold water. The precipitate formed was collected, dried under vacuum, and redissolved into warm methanol. The sludge (composed largely of oligomers) was filtered off. The filtrate was cooled to −20° C. to form a precipitate, which was recrystallized in methanol and ethyl acetate to produce a white powder, the product "BHET".

Alternatively, BHET having excellent purity may be prepared according to the following reaction scheme:

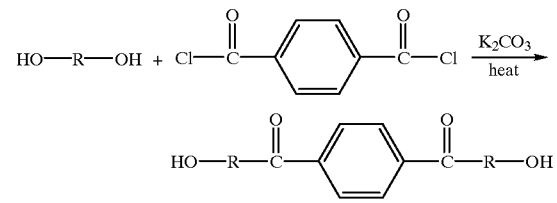

BHET is also commercially available.

Example 2

Synthesis of Poly(BHET-EP)

To a 100-ml three-necked round flask were added 9.27 g of 1,4-bis(2-hydroxyethyl)terephthalate (BHET), 8.91 g of dimethylaminopyridine (DMAP), and 30 ml of dry dichloromethane, sequentially, under dry nitrogen gas protection. The mixture was stirred with a magnetic stirring bar until a clear solution was achieved. The flask was then chilled in a dry ice/acetone bath for 10 minutes, and 5.47 g of ethyl phosphonic dichloride (EP) in 10 ml of dichloromethane was added through an addition funnel over a one-hour period. The reaction mixture was gradually heated to reflux conditions with a heating mantle and kept under reflux overnight (about 18 hours). After refluxing overnight, about 25 ml of dichloromethane was distilled off, and the remaining viscous mixture was heated up to about 90° C. with an oil bath to produce second-stage polymerization. After two hours, the remaining dichloromethane was vented, and 145 ml of chloroform was added to the flask. The resulting solution was washed three times with a saturated NaCl solution, dried over anhydrous $MgSO_4$, and poured into 500 ml of diethyl ether to precipitate the polymer product. The polymer product was collected by filtration and dried in a vacuum oven.

The GPC chromatogram shown in FIG. 1 indicated that the polymer product had an Mw of around 11.3 KD.

Example 3

Synthesis of Poly(BHET-EP/TC. 80/20)

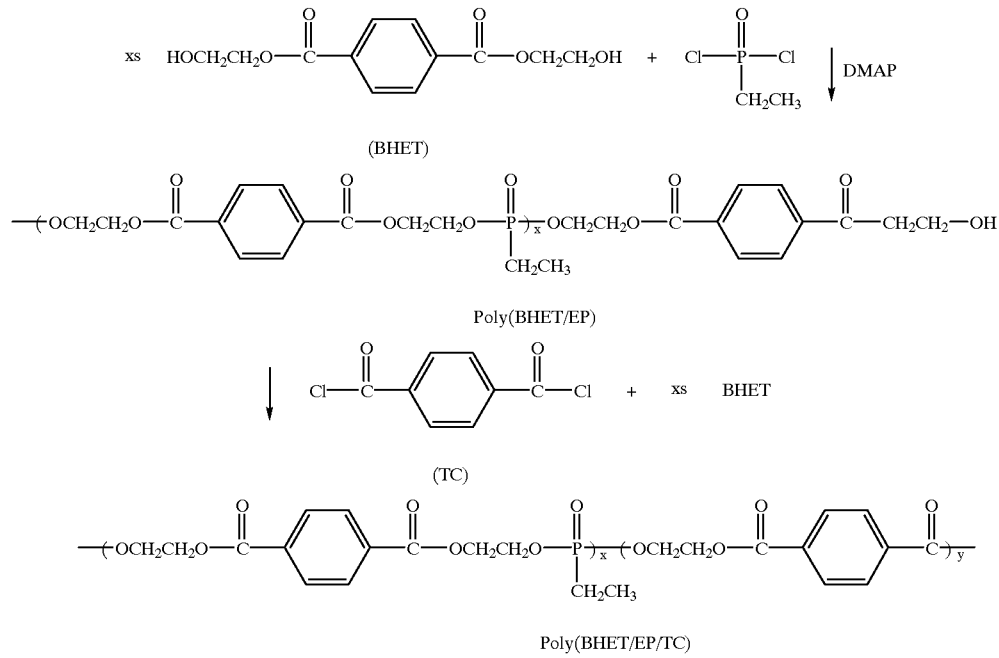

To a 100-ml, three-necked round flask were added 9.87 g of 1,4-bis(2-hydroxyethyl)terephthalate (BHET), 9.03 g of dimethylaminopyridine (DMAP), and 40 ml of dry dichloromethane, sequentially under dry nitrogen gas protection. The mixture was stirred with a magnetic stirring bar until a clear solution was achieved. The flask containing the solution was chilled in a dry ice/acetone bath for 10 minutes, and then 4.34 g of ethyl phosphonic dichloride (EP) in 15 ml of dichloromethane was added through an addition funnel over a 35-minute period. The reaction mixture was allowed to gradually warm up to room temperature and was stirred for half an hour.

The reaction mixture was then chilled in a dry ice/acetone bath, and 1.5 g of terephthalic chloride (TC) in 15 ml of dichloromethane was added over a 40-minute period. After completing the TC addition, the reaction mixture was gradually heated to reflux with a heating mantle. After refluxing overnight (about 18 hours), about 30 ml of dichloromethane was distilled off. The remaining viscous mixture was heated up to about 90° C. in an oil bath to begin the second-stage polymerization. After two hours, the remaining dichloromethane was vented off, and 150 ml of chloroform was added to the flask. The polymer solution was then washed three times with saturated NaCl solution, dried with anhydrous $MgSO_4$, and precipitated into 500 ml of diethyl ether. The resulting polymer was collected and dried in a vacuum oven.

Figure 2:
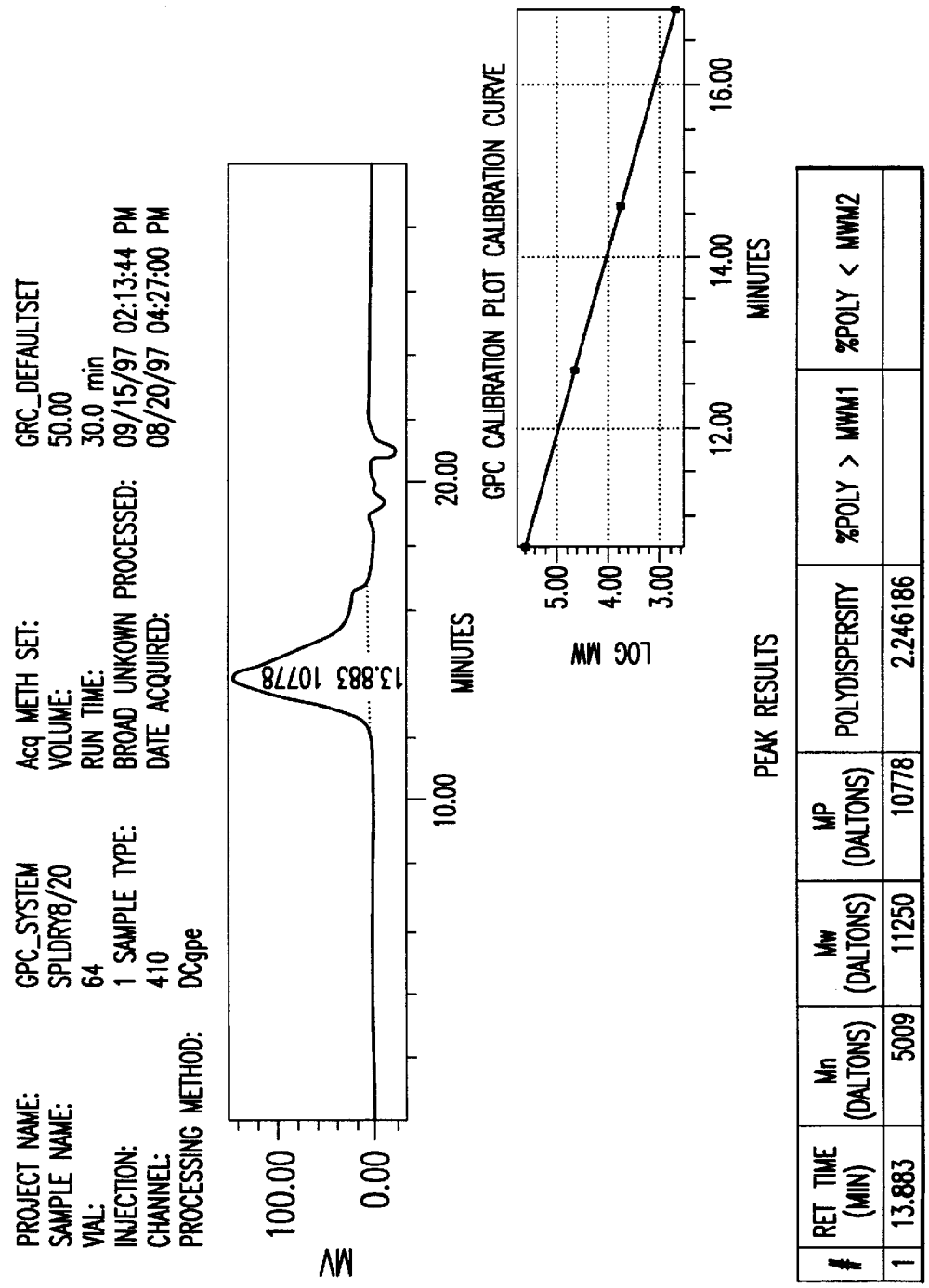
FIG. 2 shows a GPC chromatogram for poly(BHET-EP/TC) prepared in Example 3.

The GPC chromatogram shown in FIG. 2 indicated that the polymer had an Mw of 11.2 KD.

Example 4

Synthesis of Copolymers P(BHET-HP/TC, 80:20 and 90:10)

The phosphoester copolymers P(BHET-HP/TC, 80:20) and P(BHET-HP/TC, 90:10) can also be prepared by the procedure described above in Example 2, except that hexyl phosphonic dichloride (HP) is substituted for the monomer ethyl phosphonic dichloride (EP) during the initial polymerization step. In addition, the feed ratio can be varied.

Example 5

Preparation of P(BHET-EP/TC, 80/20) Microspheres Encapsulating FITC-BSA

Microspheres are prepared via a double-emulsion/solvent-extraction method using FITC-labeled bovine serum albumin (FITC-BSA) as a model protein drug. One hundred μL of an FITC-BSA solution (10 mg/mL) are added to a solution of 100 mg of P(BHET-EP/TC, 80/20) in 1 mL of methylene chloride, and emulsified via sonication for 15 seconds on ice. The resulting emulsion is immediately poured into 5 mL of a vortexing aqueous solution of 1% polyvinyl alcohol (PVA) and 5% NaCl. The vortexing is maintained for about one minute. The resulting emulsion is poured into 20 mL of an aqueous solution of 0.3% PVA and 5% NaCl while stirring vigorously. Twenty-five mL of a 2% isopropanol solution is added, and the mixture is kept stirring for one hour to ensure complete extraction.

The resulting microspheres are collected via centrifugation at 3000× g, washed three times with water, and lyophilized. Empty microspheres are prepared in the same way except that water is used as the inner aqueous phase.

The resulting microspheres are mostly between 5 and 20 μm in diameter and generally exhibit a smooth surface morphology. It is determined by observation with confocal fluorescence microscopy that the encapsulated FITC-BSA is distributed uniformly within the microspheres.

The loading level of FITC-BSA is determined by assaying for FITC after hydrolyzing the microspheres in a 0.5 N NaOH solution overnight. Loading levels are determined by comparison with a standard curve, which is generated by making a series of FITC-BSA solutions in 0.5 N NaOH. Protein loading levels of about 1 59 about 25 wt. % are readily obtained.

The encapsulation efficiency of FITC-BSA by the microspheres is determined at different loading levels by comparing the quantity of FITC-BSA entrapped with the initial amount in solution via fluorometry. Encapsulation efficiencies of about 70 % to almost 100% can be obtained.

Example 6

Preparation of P(BHDPT-EP/TC, 50/50) Microspheres Containing Lidocaine

An aqueous solution of 0.5% w/v polyvinyl alcohol (PVA) is prepared in a 600 mL beaker by combining 1.35 g of PVA with 270 mL of deionized water. The solution is stirred for one hour and filtered. A copolymer/drug solution is prepared by combining 900 mg of P(BHDPT-EP/TC, 50/50) copolymer and 100 mg of lidocaine in 9 mL of methylene chloride and vojrtex-mixing.

While the PVA solution is being stirred at 500–1000 rpm with an overhead mixer, the polymer/drug mixture is added dropwise. The combination is stirred for about one and a half hours. The microspheres thus formed are then filtered, washed with deionized water, and lyophilized overnight. The experiment yields microspheres loaded with about 3.5–4.0% w/w lidocaine.

Lidocaine-containing microspheres are also prepared from P(BHDPT-HP/TC, 50/50) by the same process. This experiment yields microspheres loaded with about 5.0–5.5% w/w lidocaine.

Example 7

In vitro Release Kinetics of Microspheres Prepared from P(BHET-EP/TC, 80/20) Copolymers Five mg of P(BHET-EP/TC, 80/20) microspheres containing FITC-BSA are suspended in one mL of phosphate buffer saline (PBS) at pH 7.4 and placed into a shaker heated to a temperature of about 37° C. At various points in time, the suspension is spun at 3000× g for 10 minutes, and 500 μl samples of the supernatant fluid are withdrawn and replaced with fresh PBS. The release of FITC-BSA from the microspheres can be followed by measuring the fluorescence intensity of the withdrawn samples at 519 nm.

Scaling up, about 50 mg of P(BHET-EP/TC, 80/20) microspheres are suspended in vials containing 10 mL of phosphate buffer saline (PBS). The vials are heated in an incubator to a temperature of about 37° C. and then shaken at about 220 rpm. Samples of the supernatant are withdrawn and replaced at various points in time, and the amount of FITC-BSA released into the samples is analyzed by spectrophotometry at 492 nm.

The results indicate generally satisfactory release rates.

Example 8

In vitro Release Kinetics of Microspheres Prepared from P(BHDPT-EP/TC, 50/50) Copolymers Approximately 10 mg of P(BHDPT-EP/TC, 50/50) microspheres loaded with lidocaine are placed in PBS (0.1 M, pH 7.4) at 37° C. on a shaker. Samples of the incubation solution are withdrawn periodically, and the amount of lidocaine released into the samples is assayed by HPLC.

The same process can be followed for microspheres prepared from P(BHDPT-HP/TC, 50/50).

The invention being thus described, it will be obvious that the same may be varied in many ways. Such variations are not to be regarded as a departure from the spirit and scope of the invention, and all such modifications are intended to be included within the scope of the following claims.

We claim:

1. A medical device comprising a biodegradable terephthalate polymer comprising the recurring monomeric units shown in formula I:

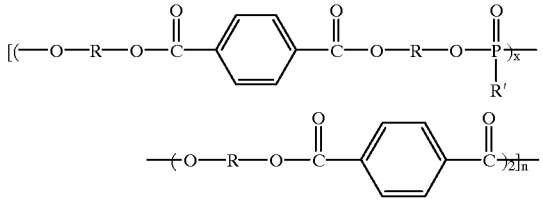

wherein R is a divalent organic moiety;
R' is an aliphatic, aromatic or heterocyclic residue;
x is ≧1; and
n is 3–7,500,
where the biodegradable polymer is sufficiently pure to be biocompatible and is capable of forming biocompatible residues upon biodegradation.

2. The medical device of claim 1 wherein R is an alkylene group, a cycloaliphatic group, a phenylene group, or a divalent group having the formula:

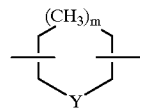

wherein Y is oxygen, nitrogen, or sulfur and m is 1 to 3.

3. The medical device of claim 1 wherein R is an alkylene group having from 1 to 7 carbon atoms.

4. The medical device of claim 1 wherein R is an ethylene group.

5. The medical device of claim 1 wherein R' is an alkyl group or a phenyl group.

6. The medical device of claim 1 wherein R' is an alkyl group having from 1 to 7 carbon atoms.

7. The medical device of claim 1 wherein R' is an ethyl group.

8. The medical device of claim 1 wherein x is from about 1 to about 30.

9. The medical device of claim 1 wherein x is from about 1 to 20.

10. The medical device of claim 1 wherein x is from about 2 to 20.

11. The medical device of claim 1 wherein said copolymer is prepared by solution polymerization.

12. The medical device of claim 1 wherein said polymer comprises additional biocompatible monomeric units.

13. The medical device of claim 1 wherein said copolymer is soluble in at least one of the solvents selected from the group consisting of acetone, dichloromethane, chloroform, ethyl acetate, DMAC, N-methyl pyrrolidone, dimethylformamide and dimethylsulfoxide.

14. The medical device of claim 1 wherein said device comprises a biologically active substance.

15. The medical device of claim 14 wherein said biologically active substance is selected from the group consisting of peptides, polypeptides, proteins, amino acids, polysaccharides, growth factors, hormones, anti-angiogenesis factors, interferons or cytokines, and pro-drugs of these substances.

16. The medical device of claim 14 wherein said biologically active substance is a therapeutic drug or pro-drug.

17. The medical device of claim 14 wherein said biologically active substance is selected from the group consisting of anti-neoplastic agents, antibiotics, anti-virals, antifungals, anti-inflammatories, anticoagulants, and pro-drugs of these substances.

18. The medical device of claim 14 wherein said biologically active substance is paclitaxel.

19. The medical device of claim 14 wherein said biologically active substance and said polymer form a homogenous matrix.

20. The medical device of claim 14 wherein said biologically active substance is encapsulated within said polymer.

21. The medical device of claim 14 wherein said polymer is characterized by a release rate of the biologically active substance in vivo partially controlled as a function of hydrolysis of the phosphoester bond of the polymer upon biodegradation.

22. The medical device of claim 14 wherein said device is adapted for implantation or injection into the body of an animal.

23. The medical device of claim 14 wherein said device results in minimal tissue irritation when implanted or injected into vasculated tissue.

24. The medical device of claim 1 wherein said device is a biosorbable suture.

25. The medical device of claim 1 wherein said device is an orthopedic appliance, bone cement, or bone wax for repairing injuries to bones and connective tissue.

26. The medical device of claim 1 wherein said device is a laminate for degradable or non-degradable fabrics or is fabricated as a tube for nerve regeneration.

27. The medical device of claim 1 wherein said device is implantable and comprises a coating comprising said polymer or is used as a barrier for adhesion prevention.

28. A biodegradable terephthalate copolymer composition comprising:
(a) at least one biologically active substance and
(b) a copolymer having the recurring monomeric units shown in formula I:

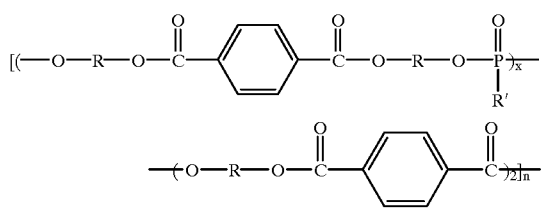

wherein R is a divalent organic moiety;
R' is an aliphatic, aromatic or heterocyclic residue;
x is $\geq 1$; and
n is 3–7,500,
where the biodegradable polymer is sufficiently pure to be biocompatible and is capable of forming biocompatible residues upon biodegradation.

29. The copolymer composition of claim 28 wherein R is an alkylene group, a cycloaliphatic group, a phenylene group, or a divalent group having the formula:

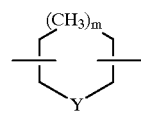

wherein Y is oxygen, nitrogen, or sulfur and m is 1 to 3.

30. The copolymer composition of claim 28 wherein R is an alkylene group having from 1 to 7 carbon atoms.

31. The copolymer composition of claim 28 wherein R' is an alkyl group or a phenyl group.

32. The copolymer composition of claim 28 wherein R' is an alkyl group having from 1 to 7 carbon atoms.

33. The copolymer composition of claim 28 wherein x is from about 1 to about 30.

34. The copolymer composition of claim 28 wherein said copolymer is prepared by solution polymerization.

35. The copolymer composition of claim 28 wherein said copolymer comprises additional biocompatible monomeric units.

36. The copolymer composition of claim 28 wherein said copolymer is soluble in at least one of the solvents selected from the group consisting of acetone, dimethylene chloride, chloroform, ethyl acetate, DMAC, N-methyl pyrrolidone, dimethylformamide and dimethylsulfoxide.

37. The copolymer composition of claim 28 wherein said biologically active substance is selected from the group consisting of peptides, polypeptides, proteins, amino acids, polysaccharides, growth factors, hormones, anti-angiogenesis factors, interferons or cytokines, and pro-drugs of these substances.

38. The copolymer composition of claim 28 wherein said biologically active substance is a therapeutic drug or pro-drug.

39. The copolymer composition of claim 38 wherein said drug is selected from the group consisting of antineoplastic agents, antibiotics, anti-virals, antifungals, anti-inflammatories, and anticoagulants.

40. The copolymer composition of claim 38 wherein said drug is paclitaxel.

41. The copolymer composition of claim 28 wherein, said biologically active substance and said copolymer form a homogeneous matrix.

42. The copolymer composition of claim 28 wherein said copolymer is characterized by a release rate of the biologically active substance in vivo controlled partially as a function of hydrolysis of the phospho-ester bond of the copolymer during biodegradation.

43. A method for the controlled release of a biologically active substance comprising the steps of:
(a) combining the biologically active substance with a biodegradable terephthalate copolymer having the recurring monomeric units shown in formula I:

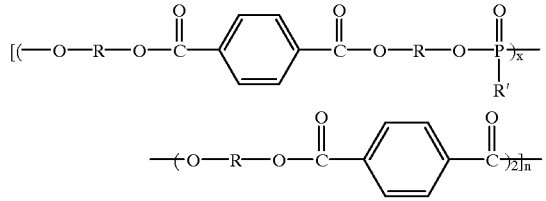

wherein R is a divalent organic moiety;
R' is an aliphatic, aromatic or heterocyclic residue;
x is $\geq 1$; and
n is 3–7,500,
where the biodegradable polymer is sufficiently pure to be biocompatible and is capable of forming biocompatible residues upon biodegradation, to form an admixture;

(b) forming said admixture into a shaped, solid article; and (c) implanting or injecting said solid article in vivo at a preselected site in an animal, such that the solid implanted or injected matrix is in at least partial contact with a bio-logical fluid.

44. The method of claim 43 wherein R is an alkylene group having from 1 to 7 carbon atoms.

45. The method of claim 43 wherein R' is an alkyl group having from 1 to 7 carbon atoms.

46. The method of claim 43 wherein x is from about 1 to about 30.

47. The method of claim 43 wherein said copolymer comprises additional biocompatible monomeric units.

48. The method of claim 43 wherein said biologically active substance is selected from the group consisting of peptides, polypeptides, proteins, amino acids, polysaccharides, growth factors, hormones, anti-angiogenesis factors and other antineoplastic agents, interferons or cytokines, and pro-drugs of these substances.

49. The method of claim 43 wherein said biologically active substance is a therapeutic drug or pro-drug.

50. The method of claim 43 wherein said drug is selected from the group consisting of chemotherapeutic agents, antibiotics, anti-virals, antifungals, anti-inflammatories, and anticoagulants.

51. The method of claim 43 wherein said drug is paclitaxel.

52. The method of claim 43 wherein said biologically active substance and said copolymer form a homogeneous matrix.

53. The method of claim 43 further comprising encapsulating said biologically active substance within said copolymer.

54. The method of claim 43 wherein said copolymer is characterized by a release rate of the biologically active substance in vivo controlled partly as a function of hydrolysis of the phosphoester bond of the copolymer upon degradation.

55. The method of claim 43 wherein said article is non-toxic and results in minimal tissue irritation when implanted or injected into vasculated tissue.

56. The method of claim 43 wherein said article is a biosorbable suture.

57. The method of claim 43 wherein said article is in the form of a laminate for degradable or nondegradable fabric, or is fabricated as a tube for nerve generation.

58. The method of claim 43 wherein said article is an orthopedic appliance, bone cement, or bone wax for repairing injuries to bone or connective tissue.

59. The method of claim 43 wherein said copolymer composition is used as a coating for an implant, or is used as a barrier for adhesion prevention.

* * * * *